United States Patent
Hubert et al.

(10) Patent No.: US 9,924,908 B2
(45) Date of Patent: Mar. 27, 2018

(54) UNOBTRUSIVE ADVISORS FOR PATIENT MONITOR

(71) Applicant: KONINKLIJKE PHILIPS N.V., Eindhoven (NL)

(72) Inventors: Volker Manfred Hubert, Gaertringen (DE); Wilhelm Meier, Herrenberg (DE); Bernd Gunter Werner Wilm, Rohrdorf (DE); Johannes Marcus Josef Eduard Bauer, Eindhoven (NL); Harald Greiner, Nufringen (DE); Benedikt Latz, Stuttgart (DE); Gerhard Tivig, Nufringen (DE); Axel Joachim Lange, Stuttgart (DE); Vitor Manuel Vicente Antunes, Herrenberg (DE); Joseph James Frassica, Gloucester, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/315,739

(22) PCT Filed: May 28, 2015

(86) PCT No.: PCT/IB2015/054012
§ 371 (c)(1),
(2) Date: Dec. 2, 2016

(87) PCT Pub. No.: WO2015/186027
PCT Pub. Date: Dec. 10, 2015

(65) Prior Publication Data
US 2017/0095217 A1  Apr. 6, 2017

Related U.S. Application Data

(60) Provisional application No. 62/008,605, filed on Jun. 6, 2014.

(51) Int. Cl.
*G08B 3/00* (2006.01)
*A61B 5/00* (2006.01)
(Continued)

(52) U.S. Cl.
CPC .............. *A61B 5/746* (2013.01); *A61B 5/044* (2013.01); *A61B 5/7475* (2013.01); *G06F 19/345* (2013.01); *G06F 19/3418* (2013.01)

(58) Field of Classification Search
CPC ....... A61B 5/746; A61B 5/044; A61B 5/7475; A61B 1/00; G06F 19/3418; G06F 19/345; G06F 1/00
See application file for complete search history.

(56) References Cited

U.S. PATENT DOCUMENTS 5,262,944 A * 11/1993 Weisner ................ A61B 5/044
128/922
5,795,301 A * 8/1998 Yasukawa .......... A61B 5/02438
482/8
(Continued)

FOREIGN PATENT DOCUMENTS

WO  2013/067495  5/2013

*Primary Examiner* — Shirley Lu

(57) ABSTRACT

A patient monitor system (10) includes a signal processor (30) which analyzes signals from physiological parameter sensors (20) to derive physiological data values, plots, and alarms. A display (12) displays physiological values and plots (42). An advisor engine, routine, or processor (34) is connected with the signal processor to analyze at least alarm occurrences, also in combination with user interactions, and provide directly actionable advice for reducing alarm frequency which is displayed unobtrusively on the display. The directly actionable advice includes specific actions or adjustments which are specific to a current patient, a present situation, or a present mode or setting of the patient monitor
(Continued)

system. The unobtrusively displayed directly actionable advice is displayed without the use requesting it.

19 Claims, 4 Drawing Sheets

(51) Int. Cl.
 *A61B 5/044* (2006.01)
 *G06F 19/00* (2018.01)

(56) References Cited

U.S. PATENT DOCUMENTS

| | | | | |
|---|---|---|---|---|
| 6,024,089 | A * | 2/2000 | Wallace | A61M 16/0051 128/204.21 |
| 6,305,372 | B1 * | 10/2001 | Servidio | A61M 16/00 128/204.21 |
| 7,606,723 | B2 * | 10/2009 | Mayaud | G06F 19/3456 600/300 |
| 8,567,393 | B2 * | 10/2013 | Hickle | G06F 19/3406 128/200.24 |
| 8,576,079 | B2 * | 11/2013 | Tanishima | G06F 19/3406 340/539.12 |
| 9,092,559 | B2 * | 7/2015 | Niklewski | G06F 19/3462 |
| 9,368,014 | B1 * | 6/2016 | Bittman | G08B 21/0453 |
| 2007/0276270 | A1 * | 11/2007 | Tran | A61B 5/0022 600/508 |
| 2008/0300572 | A1 * | 12/2008 | Rankers | A61B 5/14532 604/504 |
| 2009/0275805 | A1 | 11/2009 | Lane | |
| 2009/0275807 | A1 | 11/2009 | Sitzman | |
| 2013/0072807 | A1 * | 3/2013 | Tran | A61B 5/02405 600/485 |
| 2014/0055589 | A1 * | 2/2014 | Bangera | G06F 19/3418 348/77 |
| 2014/0088392 | A1 | 3/2014 | Bernstein | |
| 2015/0077245 | A1 * | 3/2015 | Kaufman | G06F 19/3418 340/539.12 |

* cited by examiner

UNOBTRUSIVE ADVISORS FOR PATIENT MONITOR

This application is the U.S. National Phase application under 35 U.S.C. § 371 of International Application No. PCT/IB2015/054012, filed May 28, 2015, published as WO 2015/186027 on Dec. 10, 2015, which claims the benefit of U.S. Provisional Patent Application No. 62/008,605 filed Jun. 6, 2014. These applications are hereby incorporated by reference herein.

The present application relates to the art of medical monitoring. It finds particular application in providing advice for optimizing performance unobtrusively.

Traditionally, patient monitors provide real-time readings of vital signs and other patient parameters. The readings may be provided as numbers, plots, or the like. Monitors also typically can provide trend information, e.g., plots, for each vital sign illustrating the change in the readings over time. Patient monitors traditionally provide alarms when vital signs are outside of prescribed limits and not operating properly (INOP) warnings, malfunction warnings, and the like.

Patient monitors can be tailored to many situations. However, configuring a monitor for a specific situation should be done by an experienced and authorized user to guarantee that the devices are behaving in an expected, standardized way (e.g., across the department) and to avoid safety concerns. Although some monitors do provide preconfigured profiles that can be tailored to different use models, scenarios, or patient conditions, these preconfigured profiles cover only a fraction of the detailed adjustments that can adapt the monitor to be more useful for specific patients or use conditions.

Medical technicians using a patient monitor are expected to know the behavior of the device and be able to tailor its set-up, (e.g., alarm limits) to the specific needs in a given situation (e.g., for a specific patient). However, experience has shown that the users are reluctant to tailor the set-up. For example, a smart alarm limit function can be provided which can propose alarm limits for all or individual alarms based on a patient's recent physiological parameter measurement values. While such a smart alarm is advantageous, many users do not realize that the smart alarm function is available, do not understand how to use it, and do not know how to work through all options and information that it can provide. Thus, while smart alarm limit functions are advantageous, in practice they are very rarely used and, if used, only by the most experienced users.

The automatic alarm limit function provides information related to alarms and proposes specific limits for each patient, assuming the patient is stable. However, it is not implicitly specific to the current situation and is not unobtrusive, i.e., the user needs to take action to find that the smart alarm limit function exists and to get the advice. The user needs to work through a large amount of less targeted information and needs to consider too many potential choices.

The present application overcomes these problems and others by providing advice that is directly actionable and is given unobtrusively. For example, the advice is given at the right time in the right use context for a specific issue or behavior. Unobtrusively connotes that the advice is presented to the user without the user requesting it. Directly actionable connotes that the advice proposes specific actions or adjustments which are specific to the present situation and patient in the present mode setting of the monitor. That is, the monitor is in a current mode or state to receive the suggested change in settings or the like. Minimal analysis and insight is needed by the user.

In accordance with one aspect, a patient monitor system is provided. A signal processor is configured to analyze signals from physiological parameter sensors and present physiological data values, plots, and alarms. A display is configured to display the physiological values and plots. An advisor engine, routine, or processor is connected with the signal processor to analyze at least alarm occurrences and provide directly actionable advice for reducing a frequency of alarm occurrences which is displayed unobtrusively to a user of the patient monitor system on the display.

In accordance with another aspect, a method of patient monitoring is provided. Signals from physiological parameter sensors are analyzed to derive physiological data values, plots, and alarms. The physiological values and plots are displayed on a display. At least alarm occurrences are analyzed and directly actionable advice for reducing alarm frequency is provided which is displayed unobtrusively on the display device.

One advantage resides in providing the user with pertinent advice without it being requested.

Another advantage resides in the advice being able to be acted on directly without the user needing to navigate through numerous menus and options.

Another advantage resides in giving advice which is specific to the current situation that can be used to improve or optimize performance of the patient monitor in the current situation.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
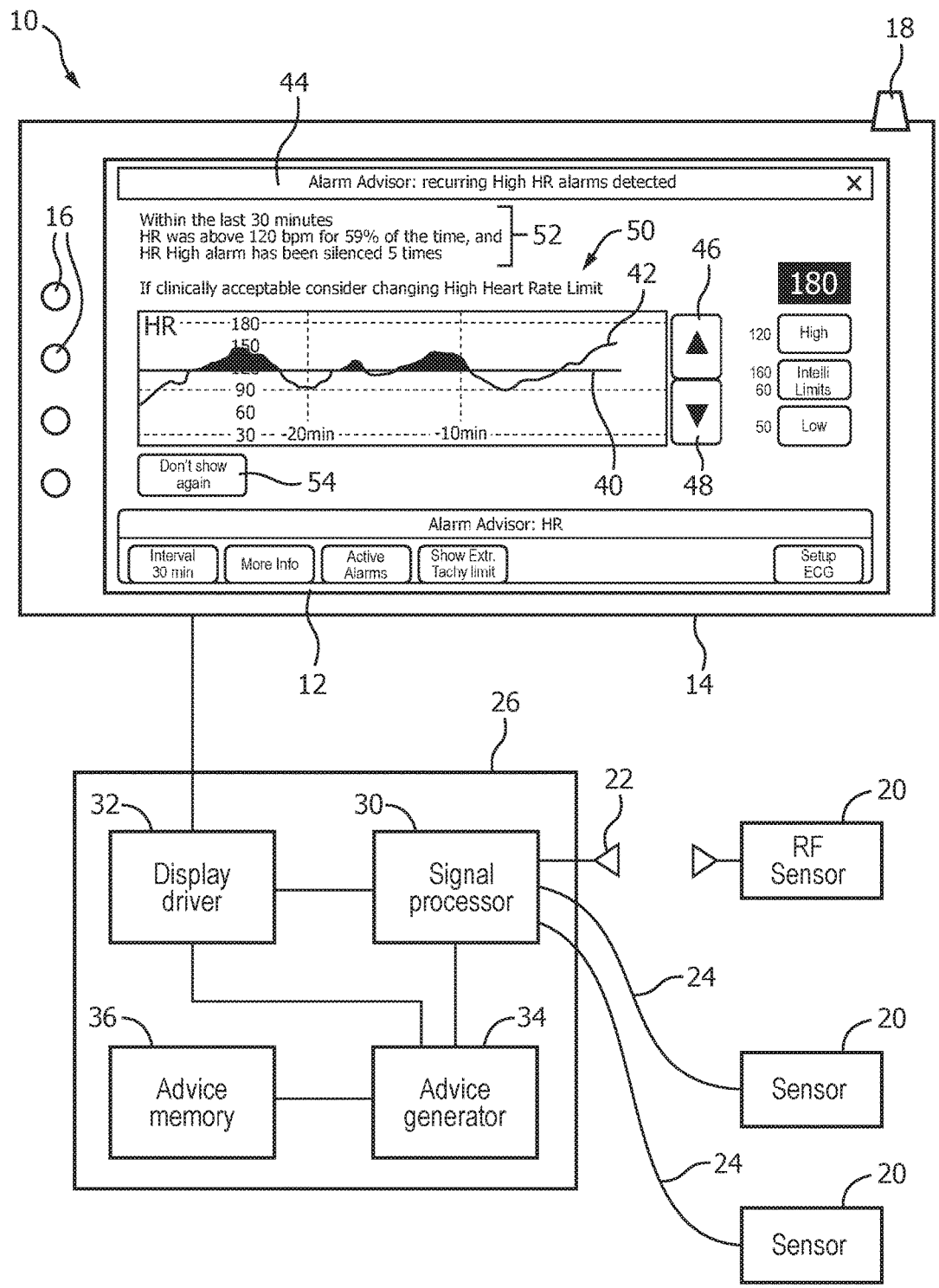
FIG. 1 is a diagrammatic illustration of a patient monitoring system including an unobtrusive advisor subsystem.

With reference to FIG. 1, a patient monitor system 10 includes a display 12 typically disposed in a housing 14. The housing and/or the display, if it is a touch-sensitive display, includes a series of user input keys or other means 16 by which the user can input instructions. The monitor system typically includes an alarm 18 such as an audio alarm or a visual alarm. The visual alarm may take form in a dedicated light source or may be part of the display. For example, the display can have a region or its background which changes color, flashes, or otherwise indicates an alarm situation.

One or more sensors 20 sense the patient's vital signs or other physiological parameters and convey the sensed parameters in the form of electrical signals, either by an RF transmission to an RF receiver 22, by cables 24, or the like, to one or more processors 26 associated with the monitor housing. For example, the one or more processors includes a signal processor or means 30 which processes the signals derived from the sensors to determine the heart rate, the respiration rate, SpO2, ECG signals, and the like. The signal processor 30 also determines when the patient parameters pass an alarm limit, such as a high heart rate alarm, a low heart rate alarm, a high respiration alarm limit, a low respiration alarm limit, a high blood oxygen limit, a low blood oxygen limit, and other vital signs and patient parameters. The signal processor 30 also determines when the quality of the received signals from the sensors is too poor to derive accurately the heart rate, respiration rate, blood oxygen rate, ECG signals, or the like, and causes an appropriate alarm to be issued. A display driver 32 converts the determined vital signs and physiological parameters, alarm limits, and the like, into appropriate format, e.g., numbers, plots, and the like, to be displayed on the display 12. The user inputs 16 include a key or other means for changing alarm limits, which changed alarm limits are communicated to the signal processor 30. An advisor engine, routine, or processor 34 (hereinafter advisor) is connected with the signal processor to identify sub-optimal patterns of use. The advisor 34 evaluates user interactions with the monitor, particularly patterns of use or user-monitor interactions indicative of sub-optimal use of the monitor. When sub-optimal use is detected, the advisor 34 retrieves appropriate instructional text from an advice memory 36 and causes it to be displayed on the display, such as in a pop-up box overlaying a region or the whole of the display surface, in a dedicated region of the display, or the like. As explained in greater detail below, the display of the advice on the monitor is triggered by a user interaction with the monitor, which is directly related to the advice being given such that it is directly actionable such that the display can be carried while the user is still interacting with the monitor sub-optimally. The advice recommends that the user take a specific action, such as advice an experienced user might give a less knowledgeable user, to enable the user to use the monitor more optimally.

Determining that the user monitor interaction is sub-optimal can take several forms. For example, the advisor can give advice to thwart potentially unwanted, non-actionable, or false alarms. As another example, in response to the user interacting with the monitor relative to an ECG signal being noisy, the advisor causes the display to advise replacing ECG electrodes, proposing different ECG leads, or the like. If the amplitude of the ECG signal is too low, particularly in the QRS area, the advisor advises selecting a different ECG lead. In response to detecting fusion beats, the advisor proposes a different ECG lead. In response to ECG signals having an elevated T-wave, the advisor again proposes a different ECG lead. The advisor can also advise performing a recalibration, e.g., reset a reference pressure. As another example, the advice may recommend checking a tube for obstructions.

The advice includes information which is specifically tailored and targeted to understand the context of the issue and to propose specific actions. For example, when the user has paused a vital sign limit alarm, the advisor causes the limit 40 and the trend of the value 42 to be displayed graphically on the display 12 and recommends adjusting the limit. The portions of the historical trend which violate the limit are highlighted to emphasize the frequency, severity, and duration of the limit violations. In this manner, the user is given an explanation of the problem along with the advice for addressing the problem. As another example, for a noisy ECG signal, a plot of the ECG signal is shown on the display 12 and the noisy portions of the ECG wave are highlighted, e.g., colorized. As another example, for fusion beats, the ECG plot is again displayed with the fusion beats highlighted. As another example, for recalibrating, the advisor generates text in a text box 44 that explains when the calibration was last done and that it should be re-calibrated within a specified time interval.

The advisor causes the display 12 to display in the text box 44 advice which is actionable, i.e., a concrete and specific suggestion how the user can easily improve the usage and configuration of the monitor. Specifically, the advisor provides advice for a user to improve the behavior of the device, such as changing the alarm limits, which is achieved by using up 46/down 48 arrows on a touch screen portion of the display 12 to raise or lower the alarm limit. As another example, the advice provides concrete recommendations for modifying or improving the application of its sensors 20. The advisor generates text or images on the display which suggest replacement or reapplication of electrodes and explain how the electrodes should be prepared for placement. This display can include a specific applicable placement diagram and indicate which of the electrodes/sensors need attention. In another example, the advisor generates recommendations for concrete modifications of the user behavior.

In another embodiment, the advice in the text box 44 may include a disclaimer 50 that the advice should be implemented only if medically appropriate. Typically, medical institutions will have protocols regarding alarm settings and the like which may require physician approval. Optionally, the advice message can be customized to the protocol to suggest that the user request physician approval to make the recommended setting change.

The advice is directly actionable by the user, i.e., the advice is given when the user is currently concerned with the issue that is causing the sub-optimal performance. That is, the advice is given at the right time and in the right use context. For example, if the user maybe due to alarm fatigue has not properly reacted to the multiple occurrences of the same alarm, the advisor can generate text recommending changing the alarm limits. Also, when the user is checking a technical alert, such as an inoperative sub-system (INOP) alert, such as a noisy or low ECG signal, and the like, the advisor 34 can control the text box 44 to display the appropriate advice or recommendation.

The advisor 34 causes the advice to be given unobtrusively, i.e., without adding a distraction or burden to the user. No extra user action is required to receive the advice. For example, the advice to adjust an alarm limit is given when the user is silencing the alarm. Advice can also be given on starting the monitor of a new patient, restarting a monitor of the patient, or the like. The advice is not given unnecessarily or too early. Rather, it is given when needed and where it is detected that the user has not taken the action without the advice being given. The advice is given when it is most probably welcome by the user. Further advice can be suppressed until there is a strong indication that the advice is needed again, or that it would be welcome again by the user. The advice is given in such a manner that it does not require any additional attention of the user. The advice does not generate any additional audible alarms or visual alarms. In connection with the timing with which the advice is given visually, other mechanisms draw the attention of the user, such as extra prompt status text, extra public windows, and the like to draw the user's attention from the currently performed task to the alert.

The advice is given unobtrusively in the sense that unnecessary advice is not given. Giving the advice may be delayed until the user has had the opportunity to decide on his/her own whether to undertake the actions to be recommended. For example, when the user has silenced or paused an alarm sufficiently often that advice to adjust the alarm limit is appropriate, the advice can be withheld until a subsequent alarm silencing to give the user the opportunity to implement the adjustment without prompting.

The advice given by the advisor is specific, e.g., in the context of the information. The advisor 34 causes only the advice or information which is needed to be displayed and in a less obtrusive way provides the opportunity to get additional relevant information. For example, the user can retrieve illustrations and text regarding recommended electrode attachment procedures. The recommendations or advice which the advisor 34 presents on the display recommends specific actions. The advice or information is given at a specific time. The advisor 34 favors specificity over sensitivity and lets the user increase or decrease the sensitivity ad hoc or by configuration to reduce the likelihood that annoying or distracting advice will be given too often. The advice is specific in the way that it stays unobtrusive. The advisor can provide a concise explanation 52 why the advice is given.

In some embodiments, different multiple advisors are provided that can follow a common user interface.

In one embodiment, the advisor 34 issues alarm limit advice. For example, the advisor 34 generates advice or recommendations for adjusting a high heart rate limit, a low heart rate limit, a high respiration rate limit, a low respiration rate limit, a high SpO2 limit, a low SpO2 limit, and the like. The advice includes recommendations for changing, e.g., increasing, a time interval over which alarms occur due to violating one of the high or low limits. The advice can also pertain to adjusting configuration agility. The advice can also relate to changing the percentage of time over which a patient parameter is monitored for violating alarm limits. Further, the advisor can instruct the user how to increase or decrease the percentage of time that the alarm must be present before advice is issued. The advisor can also look at the alarm count, particularly the number of true alarm conditions, such as initial alarm and re-alarm, and number of alarm reminders. The advisor 34 can determine the ON/OFF conditions which produce the most audible alarms. The advisor can also monitor the number of alarm silencings by the user per configured time interval. The advice can be based on the number of alarm silences during a current monitoring session or, can access the hospital patient records to assess the patient's condition. The patient's condition can be taken into account in determining the propriety of adjusting the number of silences per time interval before advice is given. The advisor can also insure that conditions in which the caregiver intentionally accepts alarm sounds, such as during a code situation, do not contribute to the count for triggering an advice display.

The advisor is reset or zeroed when a patient is discharged, such that the new patient comes in with standard alarm limits. The computation for a given high or low limit is also reset when the alarm limit is changed or when a loading profile is increased if it affects the limits. Resetting can also be done in response to leaving or closing the alarm advisor window 44, returning to the main screen, or closing the alarm limit advisory window. Resetting is also performed after reconnecting, uploading, or synchronizing settings after transport, or after a hot start.

All of the individual alarm advisors, i.e., the alarm advisor for each limit, are independently started and reset. Placing the monitor on standby does not cause a reset, nor does turning alarms off or pausing them. The trigger which is reset is the trigger which causes the advisor 34 to generate the unobtrusive notification in the advisor window 44. The user can also disable the alarm limit advisor with respect to any one or more of the limits, such as by depressing a "don't show again" key 54. Disabled alarm advisors can be re-enabled analogously or by going to the set-up menu for the alarm advisors.

The set-up menu for the high and low level advisories can be presented in various ways. In one embodiment, there is one menu page for each level. For each advisory, a series of pertinent settable values are presented, e.g., in a list. For example, for a high limit advisory, the number of high level limit alarms to be generated before an advisory is generated can be set, or the duration over which the occurrence of high level alarm limits occurs. Similar menu pages can be provided for each of the other limits.

In another embodiment, the advisor 34 includes an arrhythmia alarm advisor generator, routine, or processor. Arrhythmia alarms are not generated in response to a high or low amplitude limit. Rather, arrhythmia alarms are caused by irregularities in the heart rhythm. For some patients, the number of arrhythmia alarms is very high. On the other hand, the clinical importance of arrhythmia events has decreased with improvements in medicine and direct therapy or treatment is not necessary for most arrhythmia events. The advisor can generate advice for optimizing the alarm configuration for frequently reoccurring arrhythmia events. For example, the advice or recommendation includes switching off non-actionable alarms, adapt arrhythmia time-outs, and initiating a re-learn of the arrhythmia algorithm. When there are false arrhythmia alarms, the advice or recommendation can be to analyze the ECG lead and replace or reapply it. In addition to the text suggestion, the ECG trace is displayed with the arrhythmia portions marked, e.g., color-coded as part of the concise explanation why the recommendation is made. The presentation can include when arrhythmia alarms were triggered over the last 10, 30, 60-minutes, or the like. For pseudo-fusion beats, the ECG trace or at least the QRS complexes are shown with the fusion beat locations denoted, e.g., by color.

In another embodiment, the advisor 34 includes an ECG lead application advisor which, of course, can be in addition to the above-discussed limit alarm and arrhythmia alarm advisors. In response to the ECG signal being noisy or having an amplitude of the QRS wave that is too small, and when there is an increase in pause, asystole, or not able to analyze alarms (INOPs), the ECG lead application advisor generates advice or recommendations in the window 44 regarding how to optimize the ECG measurement, e.g., select an appropriate lead, replace a dried out electrode, optimize the lead placement, or the like. Specific portions of information from a user manual regarding correct skin preparation, and the like, or showing an application diagram can be displayed on the display 12. For example, a lead placement diagram for 3, 5, or 10-lead ECG cables and other information, such as settings for EASI versus standard lead placement or AAMI versus IEC ECG cable color schemes can be shown. The ECG lead application advisor can measure electrode impedance to determine which electrodes are good and which are bad, and appropriately mark the diagram, e.g., with a color-change, blinking, or the like. For example, bad electrodes can be marked in red and marginal electrodes in yellow. Additional information, such as the ECG trace, with an indication of noisy and clean leads, QRS amplitude per lead relative to the minimum detection level can be displayed to allow the user to comprehend the proposed advice and provide a better basis to make an informed decision.

In another embodiment, the advisor includes an alarm pause abuse advisor which, again, can be in addition to other advisors. Some users do not fully understand the difference between "silence" and "alarm pause" and "alarms OFF". Such users may select one of these options or both in order to get rid of the alarm, particularly if it is sound or noise. The advisor can be built with a specific trigger condition which detects such behavior and reports this elsewhere, e.g., to the hospital computer database, the e-mail of an advisor, an e-mail to the supervisor, or the like. In most instances, it is more appropriate to schedule training for the user during a quiet time rather than trying to train the user in a stress situation on the device itself.

Figure 2:
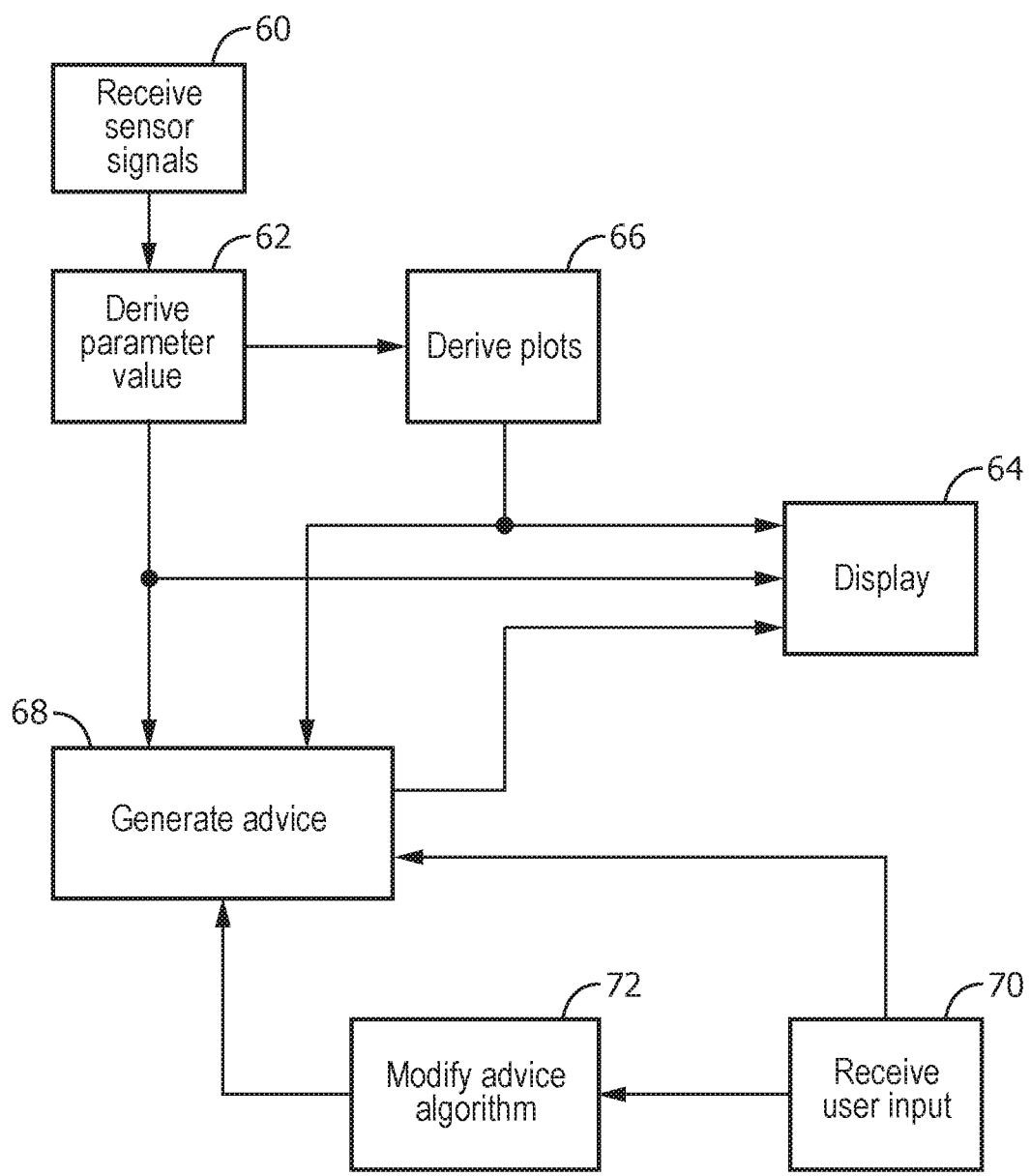
FIG. 2 is an exemplary flowchart illustrating the generation and implementation of unobtrusive advisor subsystem.

With reference to FIG. 2, the patient monitor system 10 receives vital signs or other patient parameter signals from the sensors 20 in a step or with a means 60. In a step or means 62, physiological parameter values are derived from the received vital sign or physiological parameter signals. In a step 64, a display driver 26 is caused to display the derived physiological parameter values. In a step or means 66, a plot of one or more of the physiological parameters versus time is derived for display in the displaying step 64. In a step or with a means 68, the advice is generated. More particularly, sub-optimal performance characteristics are derived from the physiological parameter values, the plots, and other inputs to be displayed during the displaying step 64. In a step or with a means 70, in response to a signal being received from the user input 16, the current interaction of the user can be derived to determine whether it is appropriate for the user to implement the advice directly. When the advice can be implemented directly, a trigger signal is generated which enables the advice message to be displayed. More specifically, the advice message is displayed when user input signals are received which show that the user is present to see the display and an appropriate time or point in the patient treatment and monitoring routine for the user to implement the advice. In a step or with a means 72, user input is also utilized to modify the advice algorithm.

In one embodiment, user interactions with the monitor are stored. For example, each time a user silences or pauses an alarm for a physiological parameter, such as heart rate, respiration rate, SpO2, blood pressure, ECG, or the like, the silencing or pausing is stored. A pattern of the interactions such as the frequency of silencing or pausing each alarm are compared with rules. For example, advice to raise an upper heart rate limit can be generated in response to the heart rate exceeding the upper limit with more than a preselected frequency, typically more than 5-10 times per hour, to reduce alarm fatigue. Based on the trend of the heart rate and the degree that the upper limit is being exceeded, the advice can include a recommendation of specifically how much to raise the upper limit. Each rule is associated with corresponding advice. The advice and the rules can be based on common sub-optimum use scenarios, such as alarm limits too high or low leading to alarm fatigue. The display of the advice is delayed as discussed above, e.g., until the user inputs suggest that the user is able to act on the advice directly. For a rule which determines if an alarm has been paused too frequently when silencing would be more appropriate, a message can be sent to a supervisor, e.g., as part of a shift report, recommending further training or instruction.

Figure 3:
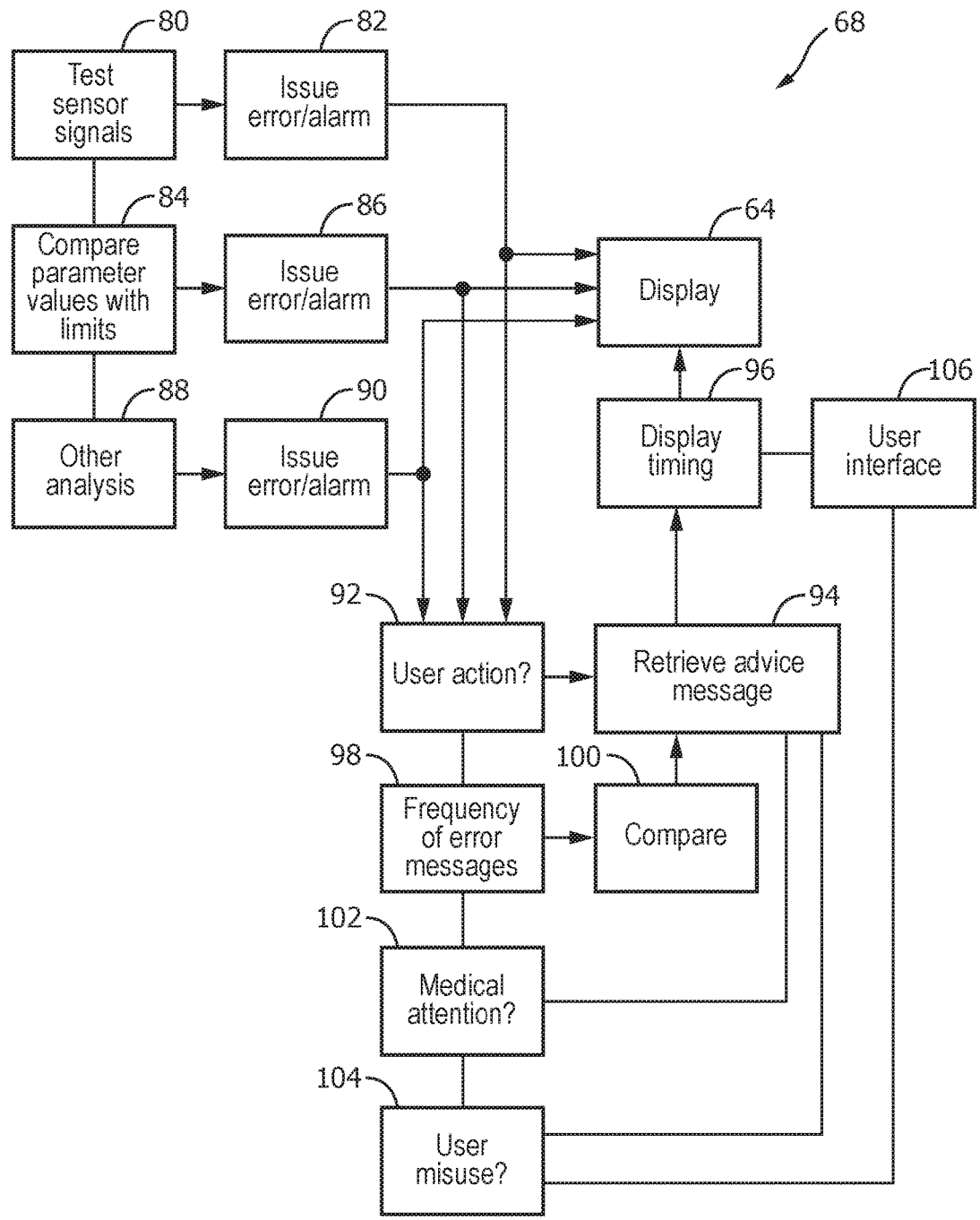
FIG. 3 is an expanded flow chart concerning generating the advice.

With reference to FIG. 3, the advice generating step or means 68 can be performed by or embodied in one or more computer processors programmed to perform steps of a method or by one or more units, modules, generators, array processors, ASICs, or other means for performing the below-described steps, and others. In a signal testing step 80, the signals received from the sensors 20 are tested for suitability, e.g., for suitable freedom from noise and sufficient amplitude for accurate processing. If one or more signals is unsatisfactory, in a step 82, an error or alarm is issued for display in the displaying step 64. In a step 84, the physiological values are compared with limits or other conditions. For example, signals, such as blood pressure, heart rate, SpO2, and the like are compared with upper and lower limits. For signals which are displayed in plots, such as trends or ECG signals, characteristics of the plot are compared with preselected standards. These standards can include various plot irregularities, such as those indicative of an arrhythmia, fusion beats, or the like. In response to detecting such plot irregularities, an error or alarm is issued in a step 86. In a step 88, various other analyses can be performed to advise the user of suboptimal performance of the patient monitor system. For example, the output of the battery may be analyzed and a low battery error or alarm can be issued in a step 90. Various other system parameters can also be analyzed, as can various other physiological parameters and appropriate errors or alarms issued.

Errors or alarms which need user action are determined in a step 92. For example, leads which are producing noisy or low amplitude output signals are identified. In a step 94, an appropriate advice message is retrieved from the advice memory 36 to be displayed in the displaying step 64. In a step 96, a decision is made whether to display the advice immediately or to delay it.

In a step 98, the frequency of error messages is determined and the determined frequency is compared with predefined standards in a step 100. For example, the number of times per thirty minutes that the heart rate exceeds a preselected high limit may be compared with a standard for the number of times for thirty minutes. In response to the standard being exceeded, an appropriate advice message is retrieved in the step 94 and displayed in the displaying step 64. For example, the retrieved advice may include a recommendation for changing, e.g., raising a high pulse rate limit. The display timing step 96 determines whether to delay displaying the advice and how long a delay. For example, if the high pulse rate limit is exceeded more than the preselected standard for times exceeded for thirty minutes, the display timing step can delay displaying the advice regarding changing the limit for a predefined duration, until the next time the limit is violated, or the like. The delay is appropriately selected to give the operator time to make the adjustment without being prompted. If the operator makes the suggested adjustment within the appropriate duration, then the advice is not displayed. In another example, the display timing step 96 monitors user inputs, such as an alarm silence input or other input indicating that the operator is present at the patient monitor, before causing the advice to be displayed in the display step 64. Moreover, the display timing step 96 can delay the display of the advice for an appropriate duration for the user to complete medically appropriate actions which are typically taken in response to the current alarm condition.

In a step 102, on a combination of the output alarms and, optionally, the monitored physiological values, a determination is made whether medical attention is needed. In response to such a determination, the appropriate advice message is retrieved in the step 94 and displayed in displaying step 64. In a step 104, a determination is made from user inputs on a user interface 106 whether the user is using the patient monitor in a suboptimal manner. For example, a determination is made whether a user is properly using "alarm silence", "alarm pause", and "alarm off" inputs. If a user is not, an appropriate message is retrieved in a step 94 and displayed. Preferably, the retrieved message is a suggestion for further training for the particular user which is displayed on the display of a supervisor rather than on the display 12 of the patient monitor system 10. FIG. 3 includes examples of common steps which are performed to generate the advice. Numerous other determinations and types of advice, such as discussed in greater detail above in conjunction with FIG. 1 are also contemplated, as are numerous other types of advice for optimizing the performance of the patient monitor system.

Figure 4:
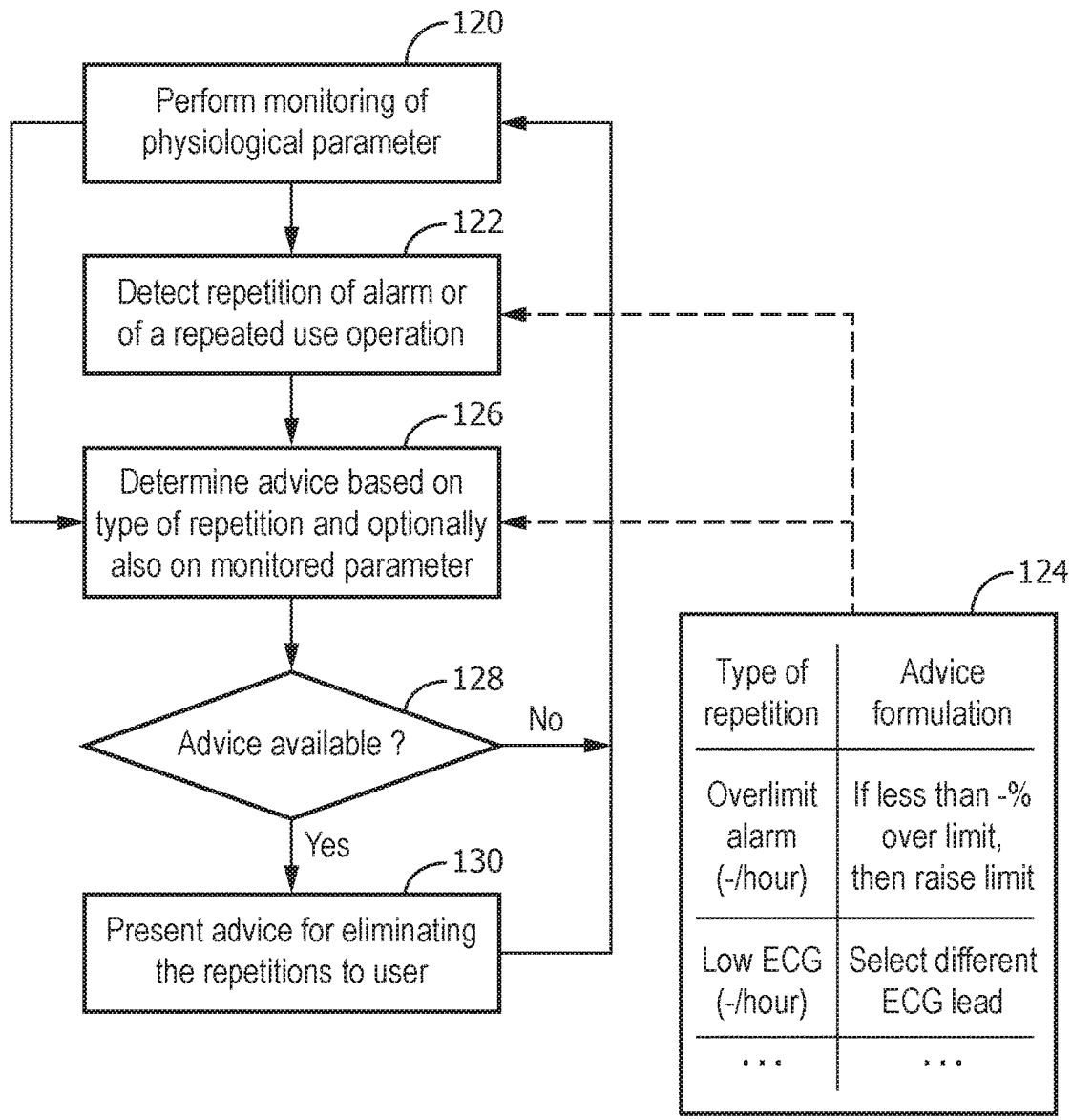
FIG. 4 is a flow chart of another embodiment for generating the advice, which is based on detecting repetitions of occurrences of an alarm or repetitions of occurrences of a user operation.

With reference to FIG. 4, another embodiment of the advice generating step or means is described, which again is suitably performed by one or more electronic processors programmed to perform the steps of FIG. 4. The approach of FIG. 4 is premised on the expectation that an operator (typically a nurse, but possibly a physician, medical technician, emergency medical service provider, or so forth) is most likely to be experiencing difficulty with the physiological monitor if the monitor experiences some repetition of the same type of alarm, or if the operator performs two or more repetitions of the same operation. In such a case, it becomes likely that the user could use advice on how to operate the monitor, and additionally providing such advice in response to a fifth (or sixth, or tenth) repetition of the same alarm or user action is likely to be considered unobtrusive and perhaps helpful for the operator. As shown in FIG. 4, in an operation 120 the physiological monitor performs monitoring of the physiological parameter of interest. During the monitoring 120, an operation 122 continually checks for a repetition of a particular type of alarm (such as an SpO2 alarm indicating the monitored SpO2 level is below a lower threshold) or a particular user operation performed on or using the physiological monitor (such as the user pressing an alarm reset button or an alarm silence button). The number of repetitions of occurrence of the alarm or user operation required to invoke the advice engine may be a configurable parameter of the advice engine, or may be hard-coded into software of the advice engine, and the number of repetitions to trigger the advice engine may in general be different for different types of alarms and/or different user operations. A typical number of repetitions to invoke the advice engine may be 5 repetitions per hour, 10 repetitions per hour, or so forth. In some cases, it is contemplated that as few as one repetition (e.g., alarm, and then a second alarm) may be sufficient to invoke the advice engine. The types of alarms and user operations whose repetition is to be detected, and the number of repetitions of each type sufficient to trigger the advice engine, are suitably stored in an advice table 124 or other data structure (or may be hard-coded).

When the operation 122 detects a sufficient number of repetitions of an alarm or user operation to invoke the advice engine, control passes to operation 126 where the advice engine is invoked to construct suitable advice (if any). The operation 126 again references the advice table 124, and chooses the advice based on the type of repetition (e.g. the type of alarm whose occurrence has repeated, e.g., 8 times in the past hour, or the type of user operation that has been repeatedly performed, e.g., 5 times in the past ten minutes, or so forth). For example, if the "low ECG signal" alarm has sounded the set number of repetitions to invoke the advice engine, then the table 124 may provide the advice "The low ECG alarm has sounded several times recently. You may want to select a different ECG lead that may provide a stronger signal." Optionally, the operation 126 may also construct the advice based on other available information such as recent history of the monitored physiological parameter. For example, if an overlimit alarm has sounded often enough to invoke the advice engine, and additionally the recent history of the monitored parameter indicates the signal was only slightly above the limit threshold for each alarm occurrence (e.g., never more than 2% above the threshold), then the advice "The overlimit alarm has sounded several times recently, with the signal being only slightly over the threshold. If medically appropriate, you may want to consider increasing the overlimit threshold by 5% in order to reduce occurrences of this alarm." On the other hand, if the signal was 10% or 20% above the overlimit threshold during at least one of the alarm events, then such advice may be unwarranted since the large 10-20% overthreshold signal may indicate a medical condition that should be investigated—in this case no advice to raise the threshold is constructed. In general, the constructed advice suggests that the user perform some action that is likely to reduce or eliminate further occurrences of the alarm that triggered the advice engine in operation 122, or suggests that the user perform some action that is likely to reduce or eliminate the need to continue to repeat the user operation whose repetition triggered the advice engine in operation 122. This reduces alarm fatigue. For example, depending upon the type of repeated alarm or user operation that is detected, the advice may include adjusting an alarm limit, adjusting ECG electrode pads, choosing a new ECG lead, increasing a signal filter setting, cleaning or replacing a fluid hose, or so forth.

In a decision 128, it is determined whether the advice engine has constructed advice in response to the detected alarm or user operation repetition. If no advice was generated, then process flow returns to monitoring operation 120 (or, in some embodiments, monitoring operation 120 is continuous and the "subsequent" operations shown in FIG. 4 are performed concurrently with the monitoring operation 120, e.g., by time multiplexing performance of the physiological monitoring and advice engine functions on a single electronic processor, or by implementing the physiological monitor and the advice engine on separate electronic processors). On the other hand, if the decision 128 determines that the advice engine has constructed advice in response to the detected repeated occurrences of the alarm or user operation, then flow transfers to operation 130 in which the constructed advice is presented to the user of the physiological monitor. The presentation of this advice is unobtrusive at least since it is likely that the user will welcome the advice after repeated occurrence of the alarm, or after having repeatedly performed the triggering user operation (apparently without achieving a desired result). The advice presentation operation 130 may also make the advice unobtrusive in other ways described herein. The advice presented in the operation 130 is also unobtrusive because it is timely, as it is presented immediately (neglecting processing time for operation 126, which is typically on the order of milliseconds or less) after the last occurrence of the repeating alarm or user operation.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:
1. A patient monitor system comprising:
a signal processor configured to analyze signals from physiological parameter sensors and present physiological data values, plots, and alarms;

a display configured to display the physiological data values and plots to a user of the patient monitor system; and an advisor engine connected with the signal processor to analyze at least alarm occurrences and provide directly actionable advice for reducing alarm occurrences, the directly actionable advice for reducing alarm occurrences comprising adjusting at least one of:
a high heart rate limit;
a low heart rate limit;
a high respiration rate limit;
a low respiration rate limit;
a high SpO2 limit; and
a low SpO2 limit;
wherein the advisor engine is further configured to:
sense user interaction; and
cause the display of directly actionable advice to be delayed based on the sensed user interaction such that the directly actionable advice is displayed unobtrusively.

2. The system according to claim 1, wherein:
the directly actionable advice proposes specific actions or adjustments which are specific to a current situation, a current patient, and a current mode setting of the patient monitor system; and
unobtrusively displaying the directly actionable advice includes displaying the directly actionable advice without the user requesting the directly actionable advice.

3. The system according to claim 1, further including:
a display driver connected with the advisor engine, the signal processor, and the display to drive the display to display physiological parameter values and plots and the directly actionable advice from the advisor engine.

4. The system according to claim 1, wherein the advisor engine is further configured to:
compare a frequency or pattern with which alarms occur and are paused or silenced to preselected alarm standards or rules.

5. The system according to claim 1, wherein the advisor engine is further configured to:
sense user interactions;
analyze the sensed user interactions relative to preselected optimal use standards and/or common sub-optimal use patterns; and
in response to the sensed user interactions being below the preselected optional use standards or indicating sub-optimal use patterns, displaying advice for improving usage of the patient monitor system on a display device.

6. The system according to claim 1, wherein the advisor engine is further configured to:
receive alarms indicative of system or physiological sensor malfunction; and
generate and display specific instructions how to resolve the malfunction.

7. The system according to claim 1, further including:
an advice memory which stores at least one of:
the directly actionable advice in text format for display on the display,
diagrams to illustrate how to implement the directly actionable advice, and,
an explanation why the advice is given.

8. The system according to claim 1, wherein the directly actionable advice for reducing alarm occurrences comprising adjusting at least one of:
a high heart rate limit; and
a low heart rate limit.

9. The system according to claim 1, wherein the directly actionable advice for reducing alarm occurrences comprising adjusting at least one of:
a high respiration rate limit; and
a low respiration rate limit.

10. The system according to claim 1, wherein the directly actionable advice for reducing alarm occurrences comprising adjusting at least one of:
a high SpO2 limit; and
a low SpO2 limit.

11. The system according to claim 1, wherein:
the advisor engine is further configured to display the advice to adjust an alarm limit when the user is silencing an alarm.

12. A method of patient monitoring comprising:
with a signal processor, analyzing signals from physiological parameter sensors and presenting physiological data values, plots, and alarms;
with one or more processors, analyzing at least alarm occurrences and generating directly actionable advice for reducing alarm occurrences, the directly actionable advice for reducing alarm occurrences comprising adjusting at least one of:
a high heart rate limit;
a low heart rate limit;
a high respiration rate limit;
a low respiration rate limit;
a high SpO2 limit; and
a low SpO2 limit;
on a display device, displaying the physiological data values and the plots and unobtrusively displaying the directly actionable advice to a user;
sensing user interaction with a patient monitor system; and
delaying displaying of the directly actionable advice based on the sensed user interaction thereby enabling direct implementation of the advice by the user.

13. The method according to claim 12, wherein the directly actionable advice proposes specific actions or adjustments which are specific to a present situation, a present patient, and a present mode setting of a patient monitoring system monitoring the patient.

14. The method according to claim 12, wherein the unobtrusively displayed directly actionable advice is displayed to the user without the user requesting the directly actionable advice.

15. The method according to claim 12, wherein analyzing the alarm occurrences includes:
comparing a frequency or pattern with which alarms occur and are paused or silenced to preselected alarm occurrence standards or rules.

16. The method according to claim 12, further including:
sensing user interactions;
analyzing the sensed user interactions relative to preselected optimal and/or sub-optimal use standards or patterns; and
in response to the sensed user interactions being below the optimal use standards or patterns, or indicative of the sub-optimal use standards or patterns, generating advice for improving usage.

17. The method according to claim 12, further including:
receiving alarms indicative of a system or physiological sensor malfunction; and
generating the directly actionable advice in the form of specific instructions how to resolve the malfunction and/or diagrams which illustrate how to implement the directly actionable advice.

18. A non-transitory computer-readable medium carrying instructions for controlling one or more processors to perform the method of claim 12.

19. A patient monitor system comprising one or more processors configured to:
- analyze signals from physiological parameter sensors and present physiological data values;
- on a display device, display the physiological data values to a user of the patient monitor system;
- analyze at least alarm occurrences and provide directly actionable advice for reducing alarm occurrences, the directly actionable advice for reducing alarm occurrences comprising adjusting at least one of:
  - a high heart rate limit;
  - a low heart rate limit;
  - a high respiration rate limit;
  - a low respiration rate limit;
  - a high SpO2 limit; and
  - a low SpO2 limit;
- determine user interaction; and
- cause the display of directly actionable advice to be delayed based on the determined user interaction.

* * * * *